United States Patent [19]

Hood et al.

[11] Patent Number: 5,045,054
[45] Date of Patent: Sep. 3, 1991

[54] APPARATUS FOR IMPLANTATION AND EXTRACTION OF OSTEAL PROSTHESES

[75] Inventors: Larry L. Hood, Laguna Hills; Robert C. Klapper, Los Angeles; James T. Caillouette, Newport Beach, all of Calif.

[73] Assignee: Advanced Osseous Technologies Inc., Aliso Viejo, Calif.

[21] Appl. No.: 475,492

[22] Filed: Feb. 6, 1990

[51] Int. Cl.$^5$ .................... A61B 17/32; A61H 1/00
[52] U.S. Cl. .................... 604/22; 128/24 A; 606/53; 606/79; 606/84; 606/99
[58] Field of Search .................... 128/24 A; 310/334; 604/22; 606/53, 79, 86, 84, 88, 99, 127, 128

[56] References Cited

U.S. PATENT DOCUMENTS

| | | | |
|---|---|---|---|
| 3,862,630 | 1/1975 | Balamuth | 128/24 A |
| 3,990,452 | 11/1976 | Murry et al. | 128/24 A |
| 4,184,510 | 1/1980 | Murry et al. | 604/30 |
| 4,248,232 | 2/1981 | Engelbrecht et al. | 128/24 A |
| 4,686,971 | 8/1987 | Harris et al. | 606/99 |
| 4,705,038 | 11/1987 | Sjostrom et al. | 604/22 |
| 4,705,500 | 11/1987 | Reimels et al. | 604/22 |
| 4,750,488 | 6/1988 | Wuchinich et al. | 604/22 |
| 4,768,496 | 9/1988 | Kreizman et al. | 604/22 |
| 4,783,656 | 11/1988 | Katz et al. | 128/777 |

FOREIGN PATENT DOCUMENTS 8802250  4/1988  PCT Int'l Appl. ............ 128/24 A

Primary Examiner—Lee S. Cohen
Assistant Examiner—Krista M. Pfaffle
Attorney, Agent, or Firm—Knobbe, Martens, Olson & Bear

[57] ABSTRACT

Apparatus particularly suited for implantation and/or extraction of osteal prostheses, comprising an ultrasonic power generator, regulator means for regulating the ultrasonic power generator in accordance with a predetermined algorithm, at least one transducer connected to the output line for converting said electrical energy to a linear mechanical motion, an acoustic transformer for increasing or decreasing peak-to-peak motion of the transducer and means for connecting the acoustic transformer to a surgical tool or a prosthetic device. The system suitably comprises a pair of transducers, one operating at each of 20 KHz and 40 KHz frequencies. Novel adapters for the four major types of osteal prosthesis are also provided.

18 Claims, 5 Drawing Sheets

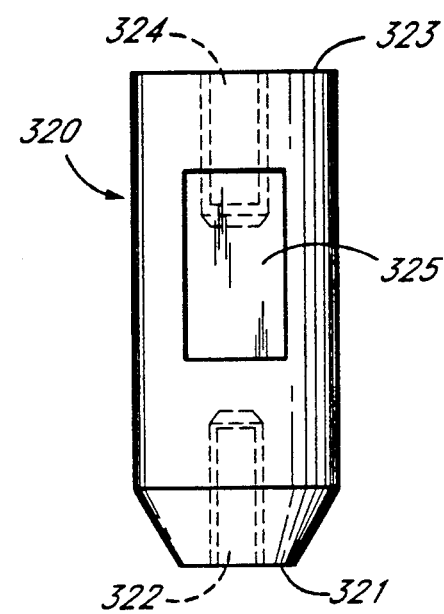
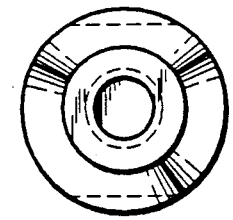
FIG. 3D
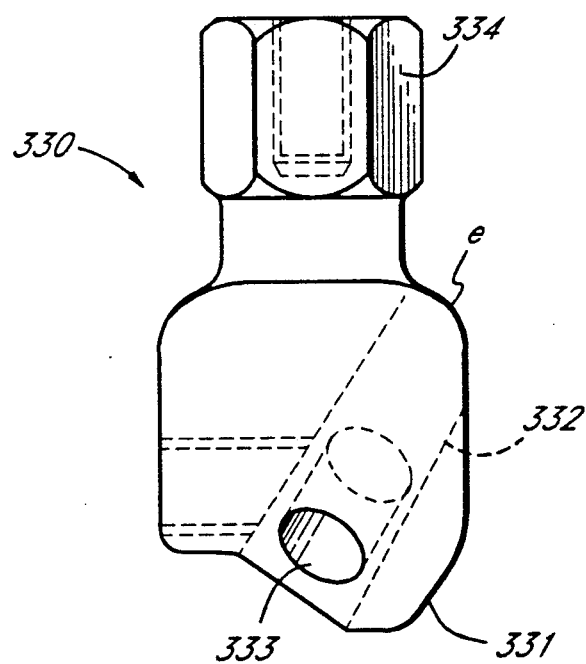
FIG. 3C
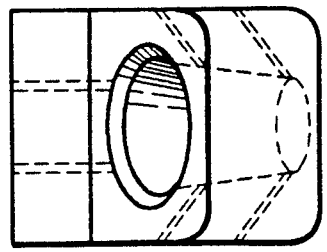

FIG. 3E
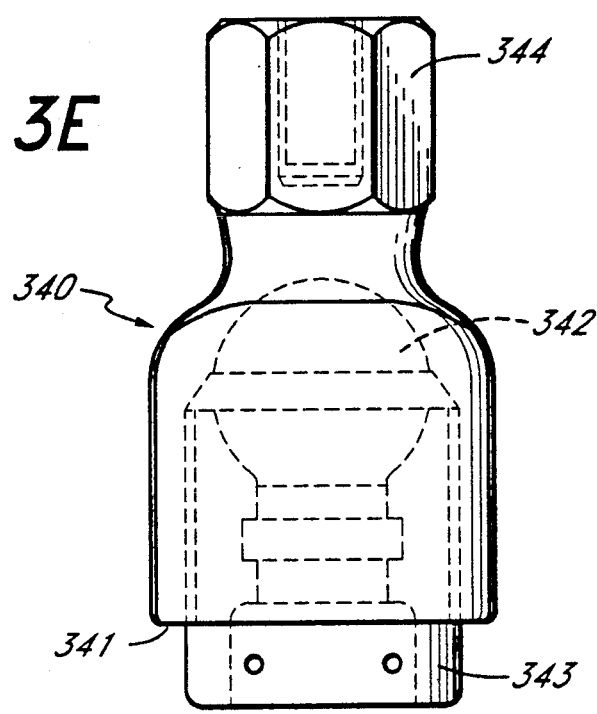
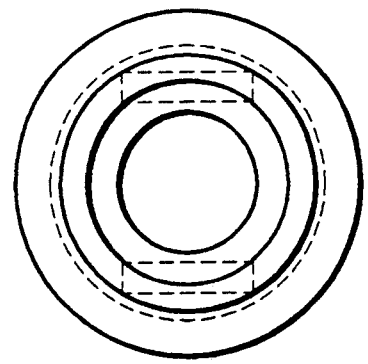
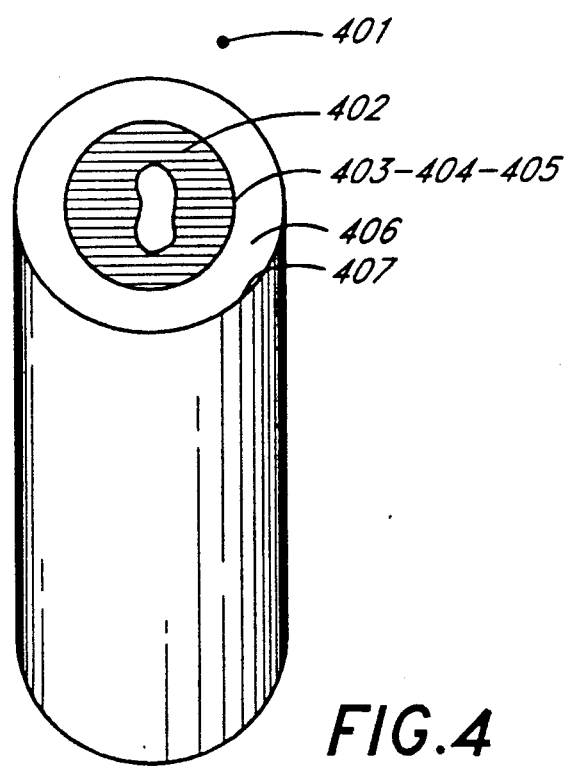
FIG. 4

APPARATUS FOR IMPLANTATION AND EXTRACTION OF OSTEAL PROSTHESES

BACKGROUND OF THE INVENTION

This application relates to an apparatus for the implantation and extraction of osteal prostheses employing an ultrasonic energy source and designed for use by orthopedic surgeons.

A variety of techniques and apparatus for implanting and removing orthopedic prostheses have been developed since replacement parts for hip joints and like were first used well over half a century ago. In particular, total joint replacements have been carried out in a large number of patients for some time. While some improvements have been made both in the techniques for implanting the prosthetic devices and in the prostheses themselves, a need remains for improved surgical procedures which are less time consuming and minimize trauma to the patient.

Revision total hip arthroplasty for replacement of defective or damaged prostheses has in particular taken on increasing importance, as the number of patients requiring such revisions increases dramatically. The procedures currently employed often result in complications, many of which are related to removal of the femoral prosthesis and the intramedullary cement mantle. The increased operating time required for revisions is associated with increased blood loss, a higher infection rate and increased postoperative morbidity. Femora perforation during cement removal, with the possibility of intraoperative or postoperative femoral fracture, is a well-known and particularly serious complication.

None of the previously available procedures for removal of the femoral prosthesis and cement mantle is entirely satisfactory. For example, while high speed cutting tools (such as the Midas Rex and Anspach pneumatic tools) have been found effective in cement removal, the use thereof may be hazardous due to the fact that the femoral cortex is easily perforated. Image intensification may reduce the risk of perforation somewhat, but is time-consuming and adds the additional risk of excessive radiation exposure. The alternative technique of controlled femoral perforation requires wide soft tissue exposure and creates multiple potential stress risers; as it has been argued that any cortical defect (including such deliberately induced perforations) could increase the chances of intraoperative or postoperative fracture, such procedure is clearly not without a potentially significant risk of serious injury to the patient.

In an effort to provide improved procedures for the removal of the femoral cement mantle, various new techniques have been developed. For example, a $CO_2$ laser has been employed for cement removal. In this context, use of a laser has been found to have some significant disadvantages. The instrumentation required is cumbersome; moreover, vaporization of the cement is slow, the fumes toxic and flammable, and the potential for thermal necrosis of endosteal bone significant. Similarly, the lithiotriptor was explored as a potential tool for fracturing the cement mantle. It was determined, however, that the shock wave is difficult to focus, and thus microfractures of adjacent cortical bone occur frequently.

Systems using ultrasonic generators in conjunction with transducer or horn elements have heretofore been developed for use in specific medical applications. A variety of ultrasonic tools are currently employed almost routinely by practitioners in a number of fields, including neurosurgery, ophthalmology and dentistry. As these devices are tailored for use in particular surgical applications, they are found to have little if any applicability outside the particular context for which they were designed.

Several systems have heretofore been developed for use in ophthalmic cataract removal, and phacoemulsification has become standard practice for removal of cataracts. In addition, "CUSA" (cavitation ultrasonic aspirator) systems have gained some currency among surgeons involved in neurological tissue resections. Ultrasonic equipment is also in current use for scaling (removal) of calcified plaque from teeth and for tissue emulsification and homogenization. All of the above-described devices are of limited applicability outside the particular context for which they were designed.

Ultrasonic devices have been employed for a variety of different applications outside the medical field as well. For example, ultrasonic apparatus has particular utility in the welding of plastics. Such equipment would also clearly be unsuitable for use in the context of surgery, where delicate living tissue must be carefully manipulated under sterile conditions.

U.S. Pat. No. 4,248,232 (Engelbrecht et al.) suggests the use of an osteotome for removal of osteal prostheses. This patent, however, is completely silent with respect to the type of osteotome which would be suitable for use in such a context. Moreover, the patent fails to indicate any parameters whatsoever for the use of an osteotome in orthopedic surgery. Therefore, it is not surprising that there has been no reported use of ultrasonic devices in the context of orthopedic surgery to date in the medical literature. In fact, since the issuance of U.S. Pat. No. 4,248,232 there has been a continued search for alternative techniques to solve the long-standing problems encountered in the removal of damaged prostheses, as well as in the implantation of new prosthetic devices. Accordingly, there remains a need for apparatus that would enable rapid and atraumatic removal of a prosthesis and/or the cement mantle surrounding same, as well as the safe and efficient implantation of prostheses.

SUMMARY OF THE INVENTION

The present invention has as its particular object the provision of an ultrasonic apparatus which is specifically designed for use by orthopedic surgeons for implantation and removal of orthopedic devices. Pursuant to the present invention, it is possible for the practitioner in the field to achieve rapid and safe explantation of prostheses of various types, including those with which a plastic cement (in particular, polymethyl methacrylate or PMMA) has been used as an adhesive or filler. Implantation of prostheses is also greatly facilitated with the inventive apparatus. Moreover, the system of the present invention is designed so as to permit use of the device by any orthopedic surgeon with minimal risk of injury to the patient after only a brief familiarization with the equipment, which is clearly not the case with the heretofore available equipment.

By virtue of the present invention, significant reductions in surgical procedure time are provided. There is also a reduction in trauma to surrounding tissues and blood loss, as well as minimization of the possibility of tissue necrosis. Further, the system operates in a manner such that the potential for weakening of the bone during the surgical procedure is reduced. As a consequence, the average hospital stay of each patient is shortened and the recovery rate increased, while the efficient use of the operating room facilities (in particular, OR floor space) and personnel is maximized. The obvious attendant benefit of all these advantages is a reduction in costs involved in the surgery as well.

Further advantages of the present invention relate to ease and security of operation. As the system has adequate reserve power to handle even the most difficult extractions, moreover, the amount of physical effort the surgeon is required to expend is reduced. The level of expertise required of the surgeon to utilize the inventive apparatus is substantially reduced, relative to that required for the complicated and often dangerous procedures heretofore necessary, in particular for successful explantations of prostheses which have been set using bone cement or when substantial bone ingrowth has occurred.

Pursuant to the present invention, direct coupling of the apparatus so as to transmit ultrasonic energy to a well fixed, cemented prosthesis allows for atraumatic removal of the prosthesis in a matter of seconds. Due to molecular friction and excitation created by transmission of ultrasonic energy, bone cement changes from a hardened state to a soft, plastic condition when contacted by ultrasonic tools. Tactile feedback facilitates distinction between the bone cement and cortical bone; in addition, the cortical bone differs greatly in molecular structure, providing an additional innate protective effect. Removal of the bone cement from the intramedullary canal can be effected atraumatically using the apparatus of the present invention, even in the case of porous implants with substantial cancellous bone ingrowth.

BRIEF DESCRIPTION OF THE DRAWINGS

FIGS. 3A-3E illustrate novel adapters for use in extraction of hip femoral prostheses in accordance with the present invention.

FIG. 4 illustrates the location of thermocouple sites on a cadaveric femur as employed in determinations of temperature during application of ultrasonic energy.

DETAILED DESCRIPTION OF THE INVENTION

Figure 1:
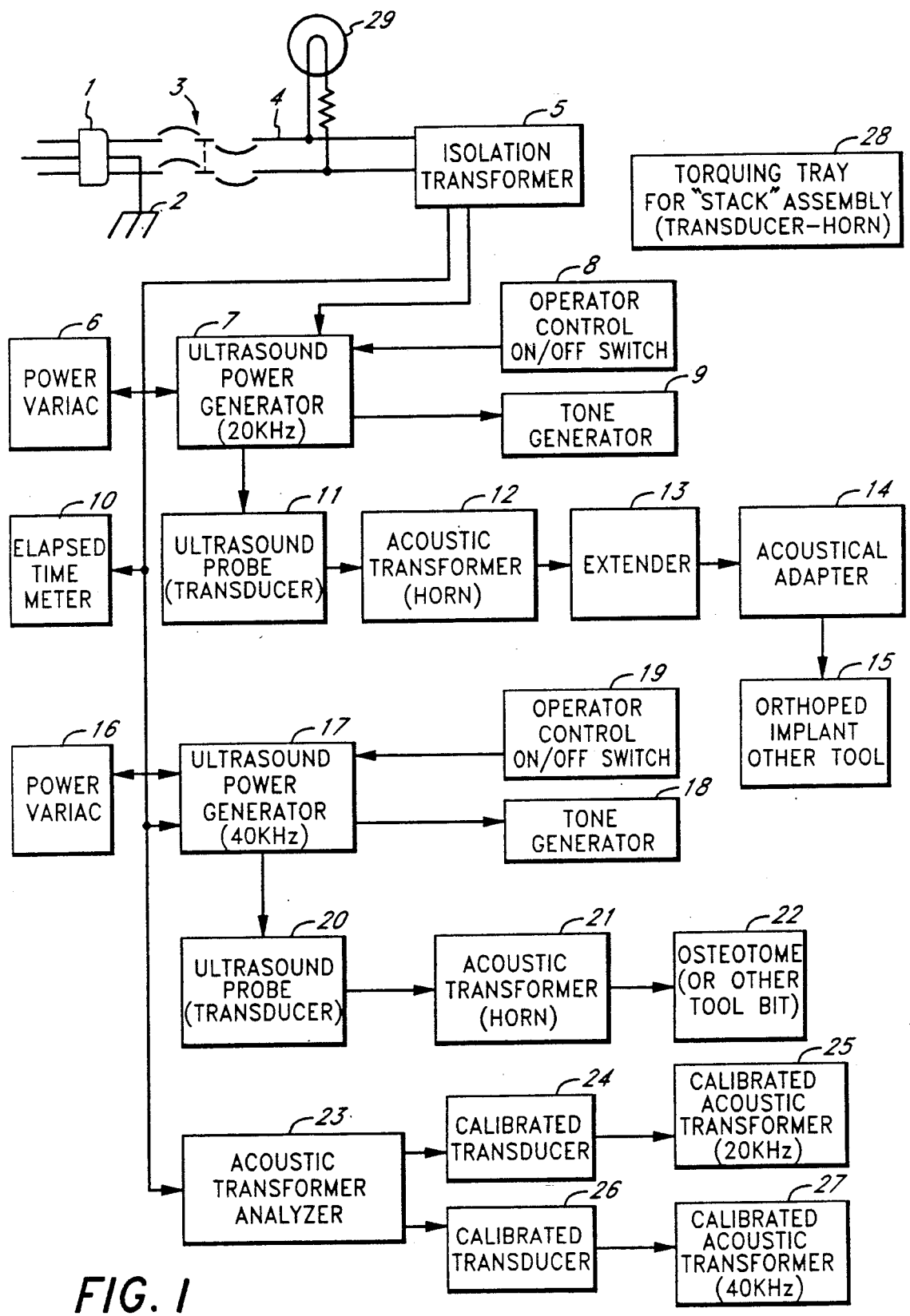
FIG. 1 illustrates in schematic form one embodiment of the inventive apparatus.
Figure 2A:
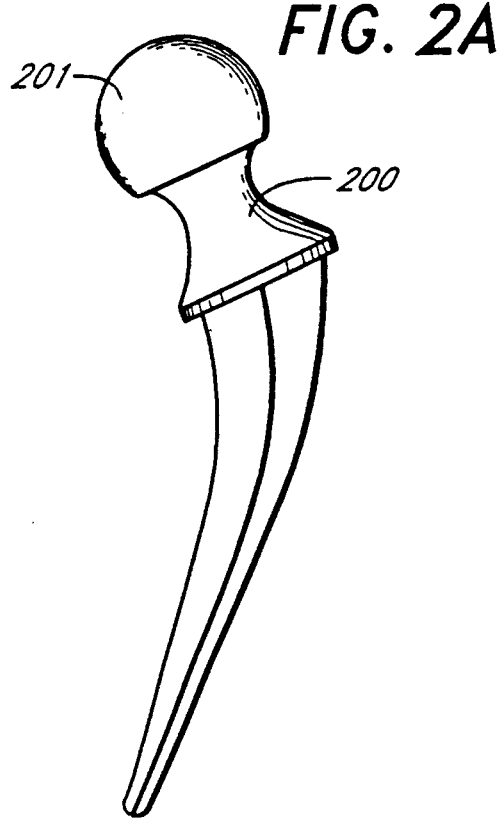
FIGS. 2A-2D illustrate four basic types of prior art hip femoral prostheses.
Figure 2B:
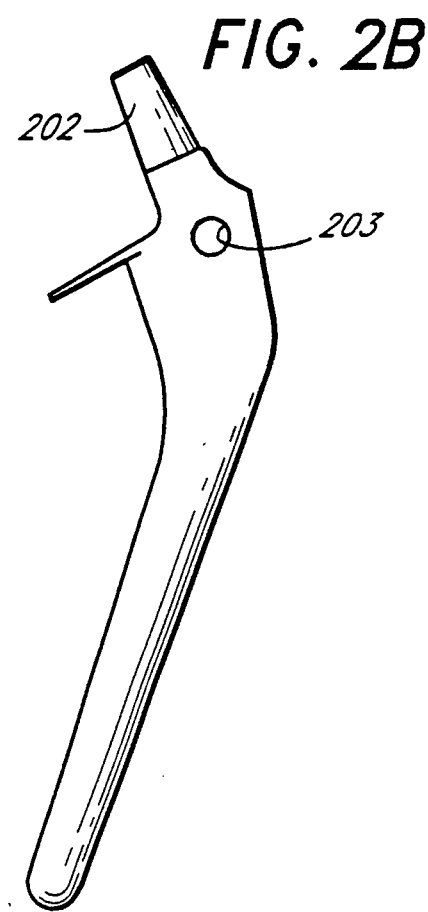
Figure 2C:
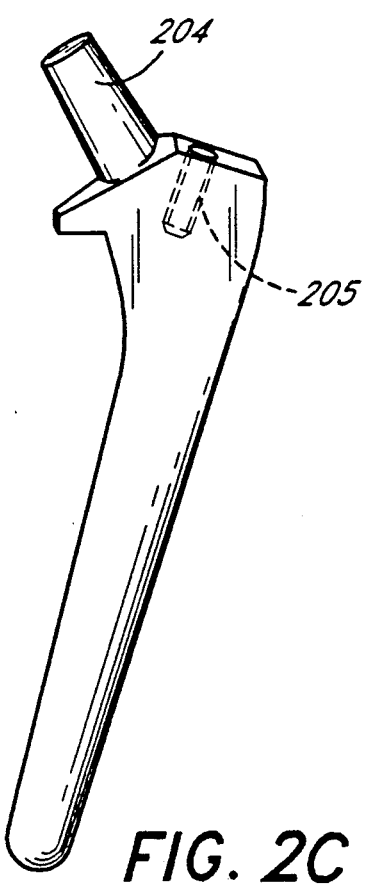
Figure 2D:
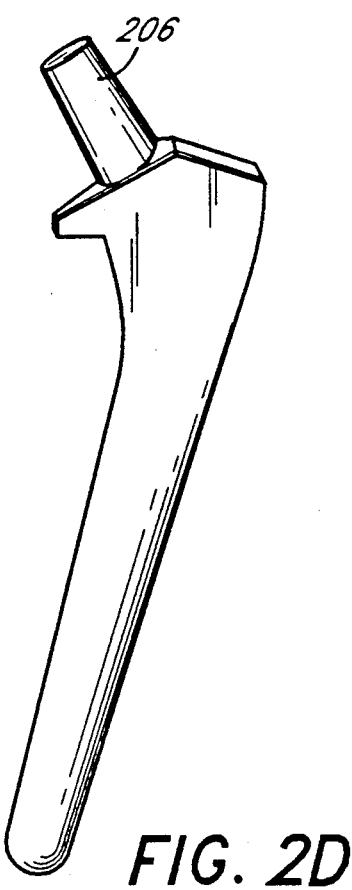

Referring to FIG. 1, there is provided in schematic form a description of one preferred embodiment of the apparatus in accordance with the present invention. A hospital grade AC electrical connector 1 (either 115V or 220V) is connected by means of low leakage AC power cable 2 to a dual circuit breaker 3 (preferably, 15A) of either the thermal or electromagnetic type. Cable 4 (generally, a low-leakage AC power cable as customarily employed for internal wiring) connects circuit breaker 3 with an ultra isolation transformer 5 for leakage and AC line noise isolation. The transformer is suitably adapted for 110-230V input (50-60 Hz). The transformer will ideally have a 1 KW rating, with less than 25.0 microamp leakage.

A regulator means 6 is provided, comprising in one embodiment a power variable auto-transformer (i.e., Variac) provided to adjust the power output limit. This device suitably has a nominal 10.0A rating. In preferred embodiments, regulator means 6 comprises control means (for example, an appropriately programmed computer and associated hardware) for regulating the ultrasonic power generator in accordance with a predetermined algorithm. Regulator means 6 is connected to ultrasonic power generator 7, which preferably has a 20 KHz center frequency. While generators are available over the range of 500-2000W, a 1 KW system is presently preferred. This is particularly the case because some well-embedded implants may require as much as 800W for the first 1 to 5 seconds of removal. Higher power generators may be of advantage in some instances, because they provide a larger bandwith of operation ($\pm$ 10% of the center frequency) at reduced power output levels. This would permit less critical matching between the generator and other elements of the system, thereby making the system easier to use. A preferred ultrasonic power system is available from Dukane, St. Charles, Ill. under the designation ULTRA 1000 AUTOTRAC; equivalent systems may of course also be employed, suitably with 115V input at about 13.0 ARMS maximum.

Control switch 8 is operative to turn on and off the high voltage generator output. A tone generator 9 is provided equipped with a commercially-available sound chip, amplifier and speaker. The tone generator 9 is operative to produce an indicator sound when the output from the ultrasonic generator 7 is on. A 60 Hz (or 50 Hz) AC elapsed time meter 10 is also provided for purposes of providing a maintenance history and for trouble shooting; a suitable time meter has an approximately 10,000 hour capacity and 0.1 hour indicator.

The high voltage generator output is connected to a transducer or ultrasound probe 11. The transducer 11 may be mounted in a handpiece (forming the transducer body) provided with a switch or operated by a medical grade footswitch. The transducer 11 may be sterilized using, e.g., ethylene trioxide; preferably, however, the transducer 11 is designed in a manner so as to be flash-steam autoclavable. Transducer 11 is designed to operate at 20 KHz (2 KW, $\frac{1}{2}$ lambda). This transducer functions as a solid state linear motor. The transducer 11 converts electrical energy to a linear mechanical motion at 20 KHZ frequency with an approximately 0.0008 inch peak-to-peak excursion. The mechanical output connection of transducer 11 is nominally a $\frac{1}{2}$-20 set screw. At 20 KHz with this design and composition, $\frac{1}{2}$ lambda is nominally 5.36 inches.

Acoustic transformer (sectional concentrator) or "horn" 12 increases or decreases the peak-to-peak motion (stroke/gain) of transducer 11. The acoustic transformer modifies not only the acoustic impedance, but also the quality factor Q. The quality factor defines a relationship between the damping factor and stroke versus the frequency shift. A high Q reflects high acoustical efficiency and minimal self-heating. Both the shape and the composition of the acoustic transformer affect Q; a straight conical acoustic transformer made of annealed 303 stainless steel, for example, would have a low Q, whereas a "stepped" horn of 7075-T6 aluminum would have a high Q. Generally, satisfactory horns are prepared from titanium or aluminum.

The length of the horn may vary greatly, depending on its design, composition and tuning frequency; typical lengths are on the order of 4.5 to 6.0 inches. For an exponential horn made from 7075-T6 aluminum, the nominal length would be 5.36 inches (½ lambda); the nominal wavelength (lambda) is the product of the density of the material and the speed of sound in the material.

Horn design is also determined by reference to the mode of operation. Thus, the shape of the horn will vary depending on whether operations are carried out in exponential (low gain), catenoidal (medium gain) or stepped (high gain) mode. One particularly suitable acoustic transformer is a 6AL-4V titanium straight conical horn with a gain of approximately 3, for a 2.4 mil peak-to-peak stroke maximum.

The acoustic transformer 12 is mechanically-acoustically connected either directly or by means of an extender 13 to an adapter 14. Extender 13 serves the purpose of physically coupling adapter 14 to horn 12, as well as to assist in matching the frequency of the transducer 11 plus the horn 12 to the combination of the extender 13, adapter 14 and an associated tool or implant. In addition, extender 13 may offer temperature isolation between the adapter 14 and horn 12, particularly when extender 13 comprises titanium. One suitable composition is 6AL4V titanium. The extender 13 may be on the order of 1 to 6 inches in length.

Adapter 14 is used to connect the apparatus to an orthopedic implant 15 (for implantation or extraction) or to individual tool bits 15 for use in various surgical applications. The primary purpose of the extender is to isolate the attached elements thermally while adjusting the nominal resonant frequency to 20 KHz ± 50 Hz.

As illustrated in FIG. 2, there are four basic types of hip femoral prosthesis in current use. Type 1 (FIG. 2A) comprises a stem 200 with a fixed ball arrangement 201; the ball generally has a diameter of 22, 26, 28 or 32 mm. A Type 2 prosthesis (FIG. 2B) has a so-called Morse taper stem 202; in addition, there is provided a horizontal extraction hole 203. The Type 3 prosthesis (FIG. 2C) comprises a Morse taper 204 and a vertical tapped hole 205. Finally, the Type 4 prosthesis (FIG. 2D) is provided simply with a Morse taper 206.

In accordance with one aspect of the present invention, novel adapters are provided which are expressly designed for use in conjunction with each of the four basic types of prosthesis depicted in FIGS. 2A-2D. The adapters are generally machined from stainless steel (e.g., 400 series), but may also be sintered, cast, etc. to the appropriate dimensions. Stainless steel is selected to lower the Q value at the implant interface while providing adequate strength to keep the adapter/implant interface from going into tension.

Figure 3A:
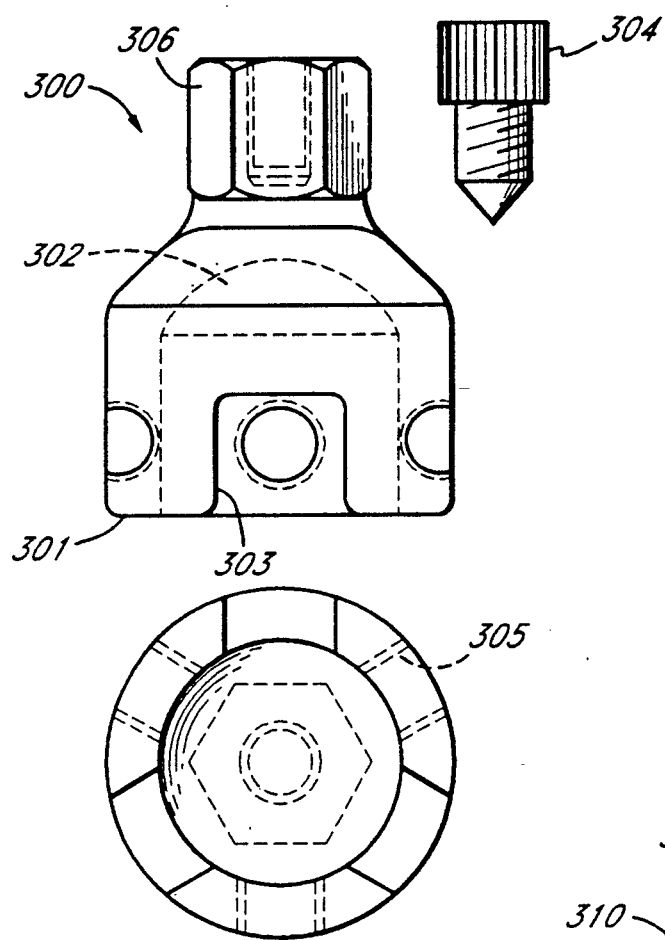

One suitable adapter for use in conjunction with a Type 1 prosthesis is illustrated in FIG. 3A. Adapter 300 comprises a base portion 301 provided with a recess 302, the diameter of which is matched closely to the diameter of the ball 201 of the corresponding Type 1 prosthesis. Suitably, the external circumference of base portion 301 is also provided with at least one recess 303 to provide clearance on the adapter 300 for a lower portion of the prosthesis 200. A plurality of cap screws 304 are provided in corresponding apertures 305 in the base portion 301. These cap screws 304 cause a high compression interference between the top of the ball 201 and the internal surface of adapter 300, as the faces of cap screws 304 contact the lower edge of ball 201 at some point below the midpoint of the diameter from the top of ball 201. In a typical arrangement, contact occurs at approximately ¾ of the diameter from the top of ball 201, whereby force is exerted at an approximate 45° vector. The cap screws 305 are generally not necessary when the adapter 300 is used for implanting. Connection means 306 is provided to permit facile assembly of adapter 300 with horn 12 and/or extender 13.

Figure 3B:
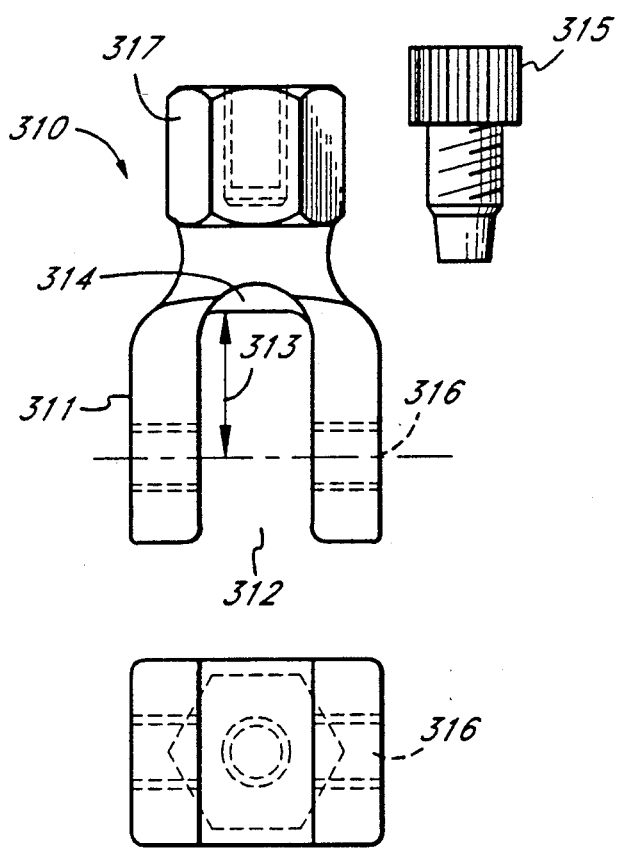

The adapter 310 illustrated in FIG. 3B is similarly designed for use in conjunction with a Type 2 implant. Base portion 311 is provided with a recess 312; portion 313 thereof is formed so as to provide a high compression fit between adapter 310 and the portion of the implant surrounding extraction hole 203. The upper portion 314 of recess 312 is designed to provide clearance for Morse taper 202. Cap screws 315 and corresponding apertures 316 in the base portion 311 are provided to engage extraction hole 203; generally, cap screws 315 are provided with tapered ends. Adapter 310 is similarly provided with attachment means 317.

FIG. 3C illustrates an adapter 320 of generally cylindrical shape for use with a Type 3 prosthesis. One end 321 is provided with an aperture 322 suitably machined to accommodate an end of a fastening means (such as a screw), the other end of which may be securely attached to the aperture 205 in the Type 3 prosthesis. End 321 is appropriately angled to provide clearance for the Morse taper 204 when adapter 320 is in place. An opposite end 323 is provided with an aperture 324, also suitably machined to permit coupling with the horn 12 and/or extender 13. To facilitate attachment and removal of adapter 320, a pair of indentations 325 (one of which is illustrated) are provided on the surface of the generally cylindrical body; indentations 325 suitably present a flat surface for secure engagement of adapter 320 by a wrench or other appropriate tool.

For use with a Type 4 prosthesis, adapter 330 (FIG. 3D) comprises a base portion 331 provided with an offset throughhole 332 at an angle to match that of the Morse taper 206. Generally, the angle of the Morse taper is on the order of 135°; throughhole 332 is matched to this angle, and offset sufficiently to match the taper in a line-line fit. A plurality of apertures 333 are provided on the circumference of base section 331 surrounding throughhole 332 for insertion of some type of fastening means (e.g., set screws) to secure Morse taper 206 in place in throughhole 332. In addition, the use of a suitable adhesive to fix Morse taper 206 in place may be advantageous. In a typical extraction procedure, adapter 330 is brought into engagement with Morse taper 206 and seated firmly, for example by tapping on surface e of adapter 330. After the setting of adhesive or other fixing agent, if any, employed to secure engagement of Morse taper 206, fastening means introduced through apertures 333 are brought into contact with Morse taper 206 so as to further strengthen the attachment of adapter 330 during the extraction procedure. Once again, neither a fixing agent nor fastening means would be necessary when the adapter is used for implantation of a prosthesis.

FIG. 3E illustrates a modified adapter 340 designed for use with a Type 1 prosthesis, and particularly suitable for implantations. While lower portion 341 is again provided with an aperture 342 designed to accommodate the ball portion 201 of the Type 1 prosthesis, the adapter 340 is further secured by means of a split nut 343, which obviates damage to the ball portion 201 of the prosthesis as might result from the use of a screw-type attachment. A bottom portion of split nut 343 with a half cup matching the diameter of ball portion 201 is first snapped into place on the prosthesis; adapter 340 including a top portion that mirrors the split nut 343 is then applied over the prosthesis and the halves of split nut 343 brought into engagement. To ensure a good alignment of the halves of split nut 343, one or more pins which are inserted into match-drilled holes may be used. Once again, connector means 344 is provided for secure engagement with horn 12 and/or extender 13.

Acoustic transformer 12, extender 13 and adapter 14 may suitably be coated with anodized (tiodized) processing, or using titanium nitride or boron nitride. Through the use of specific color coatings and/or identification codes, as well as standardized fittings for all components, the interchange of adapters and extenders for use with a variety of orthopedic implants and tool bits is rendered simple and essentially error-proof.

For implantation or removal of orthopedic prostheses, a direct mechanical/acoustical connection is made via the appropriate adapter. While the adapters are of four basic types, variations are provided to accommodate the differences encountered among the commercially available prostheses with respect to implant angle, dimensions, ball size, hole size, and composition. To facilitate use by the surgeon, the system is designed so that it is necessary merely to identify the particular type of prosthesis involved, whereupon the appropriate adapter (and, if needed, extender) may be selected from among those provided with the apparatus.

A separate circuit comprising power autotransformer 16, ultrasonic generator 17, tone generator 18, on/off switch 19, transducer 20 and acoustic transducer 21 is provided for purposes of operating an osteotome 22 or other tool bit. The elements 16-21 are of comparable design and construction as those of the first circuit described above, except that power auto-transformer 16 is designed to have a 6A maximum rating, and transducer 20 operates at 40 KHz (700W; ½ lambda=2.68 inches). Osteotome or tool sit (tip) 22 is generally of stainless steel or titanium, and is used for modifying tissue or plastic; various shapes and sizes are provided for use as gouges, curettes, drills, etc.

A calibration circuit is provided, comprising an acoustic transformer analyzer 23, a calibrated transducer 24, a calibrated acoustic transformer 25 (aluminum, precision calibrated to 20 KHz ± 20 Hz), a second calibrated transducer 26 and a second calibrated acoustic transformer 27 (precision calibrated at 40 KHz ± 40 Hz). A preferred acoustic transformer analyzer is the Dukane Model 40A350 analyzer. The calibration circuit allows for testing and calibration of elements 11-15 and/or 20-22 in whole or in part.

A torquing tray 28, generally in the form of a stainless steel tray and hold down clamps, is provided to hold the transducer firmly while assembling the various components attached thereto (i.e., the acoustic transformer, adapter/extender and the tool element). An indicator lamp 29, preferably with a voltage/current limiting resistor, advises the operator when the apparatus is on.

Operation of the system is effected as follows. For an identified prosthesis, the appropriate combination of horn, extender (if necessary) and adapter is selected. Using torquing tray 28 and suitable wrenches, the combination of horn/extender/adapter is assembled and connected with the transducer. The assembly is then connected to the prosthesis. A low power output (corresponding to a reduced stroke of, e.g., 20%) is selected for operation in a test mode and the range control is adjusted for a minimum power reading on the power meter. If the reading is greater than, e.g., 100W, adjustment is necessary before proceeding; in general, adjustment of the frequency to 20025 ± 50 Hz (for example, by change of extender) is sufficient to provide an acceptable power reading at low stroke.

Explantation may be effected by application of a suitable traction force (e.g., 10 pounds) on the transducer body housing and activation until the prosthesis has been removed (30 seconds maximum). Implantation into a femur bed already prepared for an interference fit similarly calls for application of compression force, with activation until the prosthesis is fully seated. Automatic adjustment of operating parameters is effected in a manner known per se by suitable circuitry provided within the ultrasonic generator equipment. The ultrasonic generator is designed to maintain a constant stroke. If the transducer encounters substantial clamping or holding forces, the ultrasonic generator provides additional power (up to its output limit) to keep the stroke constant. Similarly, an internal frequency control maintains a fixed phase relationship between the driving voltage and the current, to adjust for shifts in frequency due to loading. Preferably, the ultrasonic generator is designed to provide a "softstart" feature, whereby initial stress on the transducer and drive elements is reduced.

Well over one hundred different types of orthopedic implants are currently available for use in reconstruction of the hip, knee, elbow, shoulder, wrist, finger, toe, ankle, neck, etc. The inventive apparatus is designed to accommodate all of these various types of implants, simply by interchanging the adapters (and, where necessary, by using in addition the appropriate extender). Further, the apparatus may be used in conjunction with various types of T-bars (for use in removal of bone marrow), broaches, files, gouges and curettes. In fact, virtually any type of surgical tool (including those driven by hand, mallet, pneumatically, electrically or hydraulically) can be adapted for use with the present invention. Most metallic, ceramic and plastic orthopedic implants (including those fixed with bone cement and porous types with substantial bone ingrowth) may be extracted or inserted into bone. Pins and rods used for bone fixation may be driven with the inventive apparatus, as may cutting or coring cannulae and curettes for bone, tissue or plastic modification. The inventive apparatus may further be used for purposes of ultrasonic debriding. In addition, the apparatus may be used (with modified and new adapters) for dental implants, cosmetic surgery, Ob-Gyn and neurosurgical applications, etc.

In preferred embodiments, the workpiece may further comprise an irrigation/aspiration system with switch-over valves to an available hospital air vacuum line and/or a biopsy trap. For purposes of fine bone and/or tissue resection, a smaller handpiece is provided. Pneumatic-guillotine cutters (e.g., occutomes, nucleotomes, biotomes, etc.), endoprobe accessories with camera capabilities and illuminators (ideally with disposable optical fiber cables) are additional elements of the system available for particular uses. In addition to ultrasonic knives (with adjustable sharpness and drag), "hot knives" and/or uni- or bi-polar cautery electrosurgical knives may be provided.

A significant feature of a preferred embodiment of the present invention is the use of either a touch screen CRT or flat panel display to input control and data functions. In addition, the display/control system displays all systems parameters and performs the selection of appropriate adapters and/or extenders for a particular use. The system is ideally designed for infrared remote control from a sterile field and/or voice control of all system functions. In a further preferred embodiment, patient data and procedure parameter storage may be accomplished using diskettes (e.g., "floppy" disks) compatible with office or hospital computer systems. A bar code reader system may be employed. Magnetic or optical cards or disks may alternatively be used for input and/or storage of information. Repair or systems verification tests may ideally be carried out by means of modem capability of the control system.

In general, the algorithm for implantation or explantation of a particular prosthesis is initially determined empirically, in view of the complex shape of each adapter/prosthesis combination and the widely varying acoustical performance of each of the range of prostheses currently available. Once the appropriate operating parameters have been determined, this information is incorporated into the system memory so as to permit ready access by the operator/surgeon. Thus, for example, in one type of embodiment of the inventive apparatus, the operator would select the manufacturer and part number corresponding to the prosthesis in question. A display associated with the apparatus could provide an illustration of an actual-size implant for comparison purposes (e.g., with a patient X-ray) and/or identify the appropriate horn, extender and adapter for use in conjunction with the given prosthesis. Alternatively, the necessary information concerning the appropriate combination of elements for a given prosthesis could be recovered manually (e.g., using charts or tables).

To determine the appropriate configuration for any given prosthesis empirically, a first test adapter is machined to match a given implant. One of a series of standard calibrated extenders (for example, varying in length over a range of 1 to 5 inches in 0.25" increments) is attached to the adapter and to a low gain (exponential) test horn. This assembly is then attached to analyzer means and the frequency noted. In the event of a discrepancy between the measured frequency for the assembly and the target frequency of 20025 ± 25 Hz, the extender is changed and/or a new adapter is machined to an appropriate length; in practice, a difference in length of 0.001" corresponds to about 1.866 Hz. This process is repeated until frequency parameters are met.

The assembly is then attached to a calibrated power generator and transducer. At 100% stroke, the power should be less than 50 watts in free air and the stroke 1.5–4.5 mils (0.0015") peak-to-peak nominal. If the stroke is not greater than 1.0 mils peak-to-peak at all points along the stem of the implant, the horn design is modified to increase the gain.

Following the above-described procedure, it is possible to determine the ideal operating parameters for insertion or removal of any prosthesis, as well as for surgical operations using any type of tool attachment. As an example, it has been determined that explantation of a Charnley-Mueller 32 mm fixed ball total hip prosthesis required 150 watt output at an approximately 2.0 mil peak-to-peak stroke for 7 seconds; this procedure resulted in a temperature increase in the adjacent bone of less than 3° C. Implantation of the same prosthesis requires about 175 watts at the same stroke for about 3 seconds, and results in a temperature increase of about 5° C. or less. Removal of PMMA bone cement using a curette (for example, a modified Zimmer 3670 curette) requires a maximum of 125 watts at an approximately 1.5 mil peak-to-peak stroke; approximately 2 mm of material is removed per second with a temperature rise of about 7° C. or less.

In the development of the present invention, alternative technologies for explantation were also considered. One alternative was the use of an electric current source with carbon-graphite electrodes attached across an exposed metal prosthesis, whereby the heat of the current flow across the resistive metal prosthesis would eventually heat the entire prosthesis until the PMMA cement would soften and release the prosthesis. Another alternative was the use of focused ultrasound (5-100 KHz) on the centerline of the prosthesis. The energy directed from a trough-shaped or phased array of piezoceramic elements would be transmitted into the tissue through a water bag technique as presently in use for lithotripsy. A large angle, short focal length transducer shape would minimize localized tissue heating. Yet another alternative contemplated was a modified water-cooled RF welder (3 KW, 450 KHz); a special ("welding/brazing") coil shaped to selectively heat the stem portion of a prosthesis until the PMMA interface softened. All of these alternatives were rejected due to poor "fail-safe" modes of operation and/or possible undesirable clinical complications.

The invention will be better understood by reference to the following examples which are intended for purposes of illustration and are not to be construed as in any way limiting the scope of the present invention, which is defined in the claims appended hereto.

EXAMPLE 1

Prosthesis Insertion and Removal

This experiment was designed to determine the effects of ultrasonic tools and energy on endosteal bone during prosthesis and cement removal. Thermal necrosis is a common problem with various orthopaedic procedures. Temperatures above 47° C. have been shown to create irreversible bone injury in vital microscopic studies, and alkaline phosphatase denatures at 56° C. Unfortunately, temperatures as high as 100° C. have been recorded during in vitro drilling of cortical bone. To demonstrate that the apparatus of the present invention permits a safe and rapid execution of the desired surgical procedures without substantial risk of tissue necrosis, heat generation was thoroughly investigated according to the following procedure.

Ten cadaveric femurs, fresh frozen at −10° C. for 2–5 weeks, were thawed to 37° C. Thermocouple wires Type J (20 gauge) were inserted using a 2.0 mm AO drill provided with a cortical depth caliper, and silicone sealant applied to isolate the brazed tips from the water bath. Seven thermocouple sites 401–407 were employed, as illustrated in FIG. 4. Temperature and time were recorded on a 12 channel Graphtec Strip Chart Recorder (Model No. WRB 101/120), Tokyo, Japan. All channels were normalized to 37° C.; calibrations were effected at room temperature, 37° C., 46° C., and 55° C. using suitable standard laboratory thermometers before all trials, after the third trial, and at the end of all trials.

During the prosthesis insertion and removal procedures, a 40 liter galvanized tank provided with a double screw holding clamp and filled with 0.9% (normal) saline was used as a water bath. The bath was heated and maintained at 37° C. using a heat flow pump (Model No. 73T available from Polyscience Corp., Niles, Ill.

Poly(methyl methacrylate) cement (Howmedica, Rutherford, N.J.) was prepared according to the manufacturer's instructions. A 32 mm fixed head Charnley prosthesis with a double-tapered stem was inserted into each femur; a 2-4 mm cement mantle was retained.

Temperature measurement began with prosthesis insertion. After curing of the bone cement and adjustment of the cement core temperature to 37° C. each prosthesis was removed using the apparatus of the present invention, operating at 200 Watt maximum power output and 100% stroke. The forces required for removal of the prosthesis were measured using a standard 100 pound spring-type hand-held tension gauge.

In all trials except a final one, the ultrasonic coupler/prosthesis interface was tightly secured, in order to ensure efficient energy transfer and minimize the total energy requirements during removal. In the final trial, interface failure was created in an attempt to evaluate a hypothetical situation resulting in prolonged heating and ultrasonic energy transmission. After prosthesis removal, a 2.5 × 2.5 cm area of cement mantle surrounding the proximal thermocouple was removed using ultrasonic curettes and gouge, until all of the underlying bone was exposed. Temperatures were recorded throughout the removal process. Three control femurs were prepared in a similar fashion; the prostheses were inserted over a thin plastic sleeve and the prosthesis manually removed after cement curing.

Temperature measurements at the thermocouple sites during cement curing and prosthesis removal are reported in Table 1. The mean $T_{max}$ (°C.) recorded at all bone cement interface leads was 39.0 during ultrasonic removal of the prosthesis, as compared to 39.9 during cement curing. The cement core mean $T_{max}$ (°C.) was 40.8 during prosthesis removal, as compared to 47.9 during cement curing. The highest recorded cement core temperature during ultrasonic removal of a prosthesis was 43.1° C., as compared to a high of 66.3 recorded during cement curing. Temperature elevations at the mid-cortical and periosteal leads were considered negligible (<2° C.) throughout.

The mean pull-out force required for ultrasonic removal of a prosthesis was 10 pounds; the range of forces was about 8-12 pounds. The mean time required for prosthesis removal was 9.7 seconds; the range of times was about 4.2-21.0 seconds.

During the trial in which ultrasonic coupler/prosthesis failure was deliberately induced, the mean bone cement/interface $T_{max}$ was 46.5° C. Even under these unfavorable conditions, the mean pull-out force was only 22 pounds, and the time required for prosthesis removal 39.7 seconds.

The 10 human cadaveric femurs were preserved in 10% buffered formalin for 10 days prior to routine decalcification, preparation with hematoxylin and eosin, and sectioning for pathologic analysis by an experienced bone pathologist. Attention was directed to the degree of induced osteonecrosis and thermal injury which occurred during prosthesis removal (7 femurs), compared to the three controls.

Gross inspection of all specimens revealed no evidence of thermally induced eburnation of cortical bone. Curetted sites also revealed no evidence of cortical scarring.

Each specimen was analyzed by light microscopy for evidence of cellular destruction in cortical lacunae and/or altered staining patterns indicative of thermally induced matrix damage. The depth of cortical bone damage was calibrated microscopically at all interface thermocouple levels.

The mean depth of cortical damage at the cement cortical interface was determined to be 6.1 cortical damage at the curette sites was 7.0 micrometers (4.0-9.0 micrometers). Even in the trial where direct coupling to the prosthesis was deliberately suboptimal, the mean depth of cortical damage was only 14.2 micrometers (7-17 micrometers). The controls had a mean depth of cortical damage of 2.0 micrometers (0.0-3.0 micrometers).

The results confirm that direct coupling to a well-fixed, cemented prosthesis with an ultrasonic tool allows for rapid and atraumatic extraction of the prosthesis and rapid removal of the retained cement mantle without significant cortical damage. Maximum temperatures generated were far below those which generate thermal necrosis. No evidence was found of microfracture from ultrasonic energy transmission, and minimal cell injury was observed on a microscopic level. The efficiency of this technique of prosthesis removal is demonstrated by the short pull-out times and low pull-out forces required.

EXAMPLE 2

Ultrasonic Removal of Bone Cement

Eight freshly harvested canine long bone specimens (four humeri, four femoral) were prepared by exposing the intramedullary canals at the epiphysealmetaphyseal junction. The canals were broached in a standard fashion. Polymethyl methacrylate cement was prepared and digitally packed into the intramedullary canals. After curing of the cement, the specimens were allowed to harden at 10° C. for 72 hours. Ultrasonic tools were then used to remove the cement completely from an interior portion of the cement-filled area.

The bone specimens were sectioned using a diamond tip microtome into 1 mm thick disks at points near both ends of the portion from which the bone cement had been removed, as well as from a control point remote from the cement-filled area. The disks were then prepared for microradiographs and electron micrographs (20 KV, 10×). The microradiographs and electron micrographs of all disks demonstrated the preservation of normal bony architecture.

From the foregoing description, one skilled in the art can readily ascertain the essential characteristics of the invention and, without departing from the spirit and scope thereof, can adapt the invention to various usages and conditions. For example, novel problems have arisen with porous ingrowth prostheses, and removal thereof can be a highly morbid procedure involving a proximal femoral osteotomy. Early clinical applications of the present invention have provided promising results with respect to the role of ultrasonic tools in porous ingrowth revision arthroplasty. Changes in form and substitution of equivalents are contemplated as circumstances may suggest or render expedient, and although specific terms have been employed herein, they are intended in a descriptive sense and not for purposes of limitation.

TABLE I

MEAN TEMPERATURE AT THERMOCOUPLE SITES FOR HUMAN FEMORAL TRIALS

| THERMOCOUPLE SITE | CEMENT CURING Tmax (°C.) | ULTRASONIC PULL-OUT Tmax (°C.) | ULTRASONIC CURRETTING Tmax (°C.) |
| --- | --- | --- | --- |
| Proximal Interface | 40.3 | 38.9 | 38.7 |
| Mid-Prosthesis Interface | 39.5 | 39.4 | — |
| Distal Interface | 39.9 | 38.8 | — |
| INTERFACE AVERAGE | 39.9 | 39.0 | — |
| Mid-Cortex | 38.1 | 37.4 | — |
| Periosteal Surface | 37.4 | 37.6 | — |
| Cement Core | 47.9 | 40.0 | — |

What is claimed is:

1. Apparatus comprising:
   an ultrasonic power generator including an output line for transmission of electrical energy therefrom;
   regulator means for regulating said ultrasonic power generator;
   a transducer connected to said output line for converting said electrical energy to a linear mechanical motion at a first predetermined frequency;
   an acoustic transformer connected to said transducer for modulating peak-to-peak motion of said transducer;
   workpiece means for carrying out a desired manipulation, said workpiece means being selected from the group consisting of surgical tools and prosthetic devices; and
   coupling means for detachably connecting said acoustic transformer to said workpiece means, said coupling means including adapter means for isolating thermally the workpiece means connected thereto and for adjusting nominal resonant frequency in the range of 20 KHz ±50 Hz.

2. Apparatus according to claim 1, wherein said first predetermined frequency is about 20 KHz.

3. Apparatus according to claim 1, further comprising a handpiece forming a body for said transducer, said transducer being mounted therein.

4. Apparatus according to claim 3, further comprising a manual switch for operating said transducer.

5. Apparatus according to claim 3, further comprising a footswitch for operating said transducer.

6. Apparatus according to claim 1, wherein said coupling means further comprises extender means for physically coupling said adapter means to said acoustic transformer and for matching the frequency of linear mechanical motion of the transducer and the acoustic transformer to a resonant frequency for a combination of the extender means, the adapter means and the workpiece means.

7. Apparatus according to claim 1, further comprising a separate circuit including a second ultrasonic generator, a second transducer designed to operate at a second predetermined frequency, a second acoustic transformer and second coupling means for connecting said second acoustic transformer to a second workpiece means for carrying out a desired manipulation, said second workpiece means being selected from the group consisting of surgical tools and prosthetic devices.

8. Apparatus according to claim 7, wherein said second predetermined frequency is about 40 KHz.

9. Apparatus according to claim 7, wherein said second workpiece means is an osteotome comprising stainless steel or titanium.

10. Apparatus according to claim 1, further comprising a calibration circuit including an acoustic transformer analyzer connected to said ultrasonic power generator, at least one calibrated transducer coupled to said acoustic transformer analyzer, and at least one calibrated acoustic transformer coupled to said calibrated transducer and adapted for connection to a workpiece means to be calibrated.

11. Apparatus according to claim 1, wherein said regulator means further comprises control means for regulating said ultrasonic power generator in accordance with a predetermined algorithm.

12. Apparatus according to claim 12, wherein said control means further comprises input means for inputting data and control functions.

13. Apparatus according to claim 11 wherein said control means further comprises a display.

14. Apparatus according to claim 11, wherein said control means further comprises selection means for identifying appropriate coupling means for a predetermined one of said workpiece means.

15. Apparatus according to claim 11, wherein said control means is an infrared remote control.

16. Apparatus according to claim 11, wherein said control means is a voice operated control.

17. Apparatus according to claim 1, wherein said ultrasonic power generator maintains a constant stroke.

18. Apparatus according to claim 1, wherein said ultrasonic power generator includes internal frequency control means for maintaining a fixed phase relationship between driving voltage and current, thereby adjusting for shifts in resonant frequency due to loading.

* * * * *

UNITED STATES PATENT AND TRADEMARK OFFICE
CERTIFICATE OF CORRECTION

PATENT NO. : 5,045,054

DATED : September 3, 1991

INVENTOR(S) : Larry L. Hood et al

It is certified that error appears in the above-identified patent and that said Letters Patent is hereby corrected as shown below:

Column 12, line 3, insert --The mean depth of cortical damage at the cement cortical interface was determined ot be 6.1 micrometers (0.0-12.0 micrometers)."--.

Column 12, lines 3-4, delete "cement cortical interface was determined to be 6.1 cortical damage at the"--.

Column 13, line 12, Table 1, reads "Interface 39.9 39.0" should read

```
          INTERFACE
--        AVERAGE        39.9        39.0        --
```

Signed and Sealed this

Twenty-first Day of December, 1993

Attest:

BRUCE LEHMAN

*Attesting Officer*  *Commissioner of Patents and Trademarks*